(12) United States Patent
Malhotra et al.

(10) Patent No.: US 11,234,981 B2
(45) Date of Patent: Feb. 1, 2022

(54) COMBINATION THERAPY FOR USE IN TREATING RETROVIRAL INFECTIONS

(71) Applicant: CIPLA LIMITED, Mumbai (IN)

(72) Inventors: Geena Malhotra, Mumbai (IN); Kalpana Joshi, Thane (IN); Preeti Raut, Mumbai (IN)

(73) Assignee: Cipla Limited, Mumbai (IN)

(*) Notice: Subject to any disclaimer, the term of this patent is extended or adjusted under 35 U.S.C. 154(b) by 66 days.

(21) Appl. No.: 16/606,021

(22) PCT Filed: Apr. 18, 2018

(86) PCT No.: PCT/IN2018/050229
§ 371 (c)(1),
(2) Date: Oct. 17, 2019

(87) PCT Pub. No.: WO2018/193470
PCT Pub. Date: Oct. 25, 2018

(65) Prior Publication Data
US 2020/0046701 A1    Feb. 13, 2020

(30) Foreign Application Priority Data
Apr. 18, 2017 (IN) .............................. 201721013733

(51) Int. Cl.
| | | |
|---|---|---|
| A61K 31/519 | (2006.01) | |
| A61K 31/506 | (2006.01) | |
| A61K 31/513 | (2006.01) | |
| A61K 9/28 | (2006.01) | |
| A61K 31/4439 | (2006.01) | |
| A61K 31/4525 | (2006.01) | |
| A61K 31/675 | (2006.01) | |

(52) U.S. Cl.
CPC .............. *A61K 31/513* (2013.01); *A61K 9/28* (2013.01); *A61K 31/4439* (2013.01); *A61K 31/4525* (2013.01); *A61K 31/675* (2013.01)

(58) Field of Classification Search
CPC ................ A61K 31/519; A61K 31/506; A61K 31/4439; A61P 31/18
USPC ...................... 514/262.1, 269, 340
See application file for complete search history.

(56) References Cited

U.S. PATENT DOCUMENTS

2008/0200435 A1    8/2008   Stoffels

FOREIGN PATENT DOCUMENTS

| CN | 101060844 A | 10/2007 | | |
|---|---|---|---|---|
| IN | 201721913733 A | 4/2017 | | |
| WO | 03084462 A2 | 10/2003 | | |
| WO | 2005021001 A1 | 3/2005 | | |
| WO | 2011120133 A1 | 10/2011 | | |
| WO | 2017095761 A1 | 6/2017 | | |
| WO | 2017138022 A1 | 8/2017 | | |
| WO | WO 2018-039157 A1 * | 3/2018 | ............. | A61K 31/52 |
| WO | 2018193470 A1 | 10/2018 | | |

OTHER PUBLICATIONS

Ray, Adrian S. et al., "Tenofovir alafenamide: A novel prodrug of tenofovir for the treatment of Human Immunodeficiency Virus", Antiviral Research, 2016, pp. 63-70, vol. 125. Elsevier B.V.
Anderson, Matt S. et al., "A Two-Way Steady-State Pharmacokinetic Interaction Study of Doravirine (MK-1439) and Dolutegravir", Clinical Pharmacokenetics, 2017, pp. 661-669, vol. 56, No. 6, Springer.
Anderson, Matt S. et al., "Safety, tolerability and pharmacokinetics of doravirine, a novel HIV non-nucleoside reverse transcriptase inhibitor, after single and multiple doses in healthy subjects", 2015, pp. 397-405, vol. 20, International Medical Press.
Prakash, Swati et al., "Bioenhancement Effect of Piperine and Ginger Oleo Resin on the Bioavailability of Atazanvir", International Journal of Pharmacy and Pharmaceutical Sciences, 2015, pp. 241-245, vol. 7, No. 10, Innovare Academic Sciences.
Kasibhatta, Ravisekhar, et al., "Influence of Piperine on the Pharmacokinetics of Neverapine under Fasting Conditions: A Randomized, Crossover, Placebo-Conlrolled Study", Drugs R D, 2007, pp. 383-391, vol. 8, No. 6 Adis Data Information BV.
Sherman, Elizabeth M. et al., "Cobicistat: Review of a Pharmacokinetic Enhancer for HIV Infection". Clinical Therapeutics, 2015, pp. 1876-1893, vol. 37, No. 9, Science Direct.
Elion, Richard et al., "Phase 2 study of cobicistat versus ritonavir each with once-daily atazanavir and fixed-dose emtricitabine/tenofovir df in the initial treatment of HIV infection". AIDS, 2011, pp. 1881-1886, vol. 25, No. 15, Lippincott Williams & Wilkins.
Foreign communication from a related application—International Preliminary Report on Patentability, Application No. PCT/IN2018/050229, dated Oct. 22, 2019, 9 pages.
Foreign communication from a related application—International Search report and Written Opinion, Application No. PCT/IN2018/050229, dated Jul. 3, 2018, 13 pages.
Ananworanich, Jintanat et al., "Failures of 1 week on, 1 week off antiretroviral therapies in a randomized trial", AIDS, 2003, pp. F33-F37, vol. 17, Lippincott Williams & Wilkins.
Kesarwani, Kritika, et al., "Bioavailability enhancers of herbal origin: An overview," Asian Pacific Journal of Tropical Biomedicine, 2013, pp. 253-266, vol. 3, No. 4.
Foreign communication from a related application—Official Action dated Jul. 1, 2021, issued in Chinese Application No. 201880040368.7, including English Translation, 14 pages.

\* cited by examiner

*Primary Examiner* — Charanjit Aulakh
(74) *Attorney, Agent, or Firm* — Conley Rose, P.C.; Rodney B. Carroll

(57) ABSTRACT

A pharmaceutical composition is provided comprising combination of antiretroviral drugs optionally in combination of pharmacokinetic boosters. The formulation is used for the treatment of diseases caused by retroviruses. The process of preparation of the formulation is also provided.

23 Claims, No Drawings

COMBINATION THERAPY FOR USE IN TREATING RETROVIRAL INFECTIONS

CROSS REFERENCE TO RELATED APPLICATIONS

This application is a filing under 35 U.S.C. 371 of International Application No. PCT/IN2018/050229 filed Apr. 18, 2018, entitled "Combination Therapy for Use in Treating Retroviral Infections" which claims priority to Indian Provisional Patent Application Serial Number 201721013733 filed on Apr. 18, 2017 which applications are incorporated by reference herein in their entirety.

FIELD OF INVENTION

The present invention relates to pharmaceutical composition comprising at least one antiretroviral agent and optionally at least one pharmacokinetic booster or enhancer and optionally at least one pharmaceutically acceptable excipients. The present invention also provides manufacturing processes thereof and use of the said composition for prevention, treatment or prophylaxis of diseases in the patients in need thereof.

BACKGROUND AND PRIOR ART

In 1981, a sudden increase of Kaposi's sarcoma was reported amongst young homosexual men. The causative agent of AIDS was found out to be a retrovirus; which was called 'human immunodeficiency virus' (HIV). HIV enters predominantly helper T cells of the human immune system by binding to CD4 receptors. HIV kills the CD4 positive immune cells that it infects, thereby crippling the immune system. HIV can be transmitted through unprotected sexual intercourse, intravenous drug use with contaminated injection needles, transfusion of HIV-infected blood, and by mother-to-child-transmission during pregnancy, delivery and breast feeding.

In 2008, AIDS killed approximately 2.0 million people while in the same year, 2.7 million people were newly infected with HIV. By the end of 2008, 33.4 million people were living with the virus, more people than ever before. The continuing rise in the number of HIV-infected patients is not only the result of continued high rates of new HIV-infections. It is also a reflection of the beneficial impact of increased global access to antiretroviral therapy. Second, the number of new HIV infections has decreased from a peak of 3.6 million in 1996 to 2.7 million in 2008. The number of AIDS-related deaths has declined from 2.2 million in 2004 to 2.0 million in 2008.

With the advent of highly active antiretroviral therapy (HAART), HIV-1 infection is now manageable as a chronic disease in patients who have access to medication and who achieve durable virologic suppression. The key to the success of HAART in some patients lies in the drug combination's ability to disrupt HIV at different stages in its replication. HIV cannot be completely cured but its progression can be controlled. Currently known HIV drug classes are HIV reverse transcriptase inhibitors, protease inhibitors, entry inhibitors (also known as fusion inhibitors), integrase inhibitors and viral DNA polymerase inhibitors. There are two types of reverse transcriptase inhibitors-nucleoside and non-nucleoside.

Currently available antiretroviral drugs for the treatment of HIV include: zidovudine or AZT (Retrovir®), didanosine or DDI (Videx®), stavudine or D4T (Zenith®), lamivudine or 3TC (Epivir®), zalcitabine or DDC (Hivid®), abacavir sulphate (Ziagen®), tenofovir disoproxil fumarate (Viread®), emtricitabine (Emtriva®), Combivir® (contains 3TC and AZT), Trizivir® (contains abacavir, 3TC and AZT), Epzicom® (contains abacavir and lamivudine); nevirapine (Viramune®), delavirdine (Rescriptor®), efavirenz (Sustiva®), saquinavir (Invirase®, Fortovase®), indinavir (Crixivan®), ritonavir (Norvir®), nelfinavir (Viracept®), amprenavir (Agenerase®), atazanavir (Reyataz®), Evotaz® (contains atazanavir and cobicistat), fosamprenavir (Lexiva®), Kaletra® (contains lopinavir and ritonavir), enfuvirtide (T-20, Fuzeon®), Truvada® (contains Tenofovir and Emtricitabine), darunavir (Prezista®), Prezcobix® (contains darunavir and cobicistat), dolutegravir (Tivicay®), Triumeq® (contains dolutegravir, abacavir and lamivudine), elvitegravir (Vitekta®), Genvoya® (contains elvitegravir, cobicistat, tenofovir alafenamide fumarte and emtricitabine), Stribild® (contains elvitegravir, cobicistat, tenofovir disoproxil fumarte and emtricitabine) raltegravir (Isentress®), Complera® (contains emtricitabine, tenofovir disoproxil fumarte, rilpivirine) and Atripla® (contains fixed-dose triple combination of tenofovir, emtricitabine and efavirenz).

Although the use of combination drug therapies against HIV has proven to be effective in many patients, the current drug regimens are far from ideal. Treatment failure often (though not always) occurs because a patient's strain of HIV may develop resistance to one or more of antiretroviral medications. The manner by which HIV develops resistance to antiretroviral drugs is similar to the way in which bacteria or mycobacterium develops resistance to antibiotics: for example selection of insufficiently potent drug therapy for mutant strains that are resistant to the medications administered to the patient. These mutant strains then replace the wild-type strain due to their selective replication advantage in the face of drug pressure, leading to treatment failure.

Further the success of HAART depends on patient related factors as well, the most important being adherence. The HIV therapy is a life-long therapy coupled with high levels of adherence to the same. This is rather a demanding task for HIV infected patients due to various reasons such as low morale, social stigma, low immunity attributed to the disease. Some studies have also shown that adherence to prescribed drugs over long treatment periods is generally poor. (Jintanat A. et al. Swiss HIV Cohort Study. Failures of 1 week on, 1 week off antiretroviral therapies in a randomized trial AIDS, 2003; 17:F33-F37).

Hence, such non-adherence may lead to rebound in viral replication and, in presence of sub-optimal drug concentration may lead to rapid development of drug resistance. This development of drug resistance may be disastrous because of the complexity and cost associated with second line regimens and the potential for transmission of drug resistant virus in the community.

The therapy may involve use of different drug combinations, which are difficult to adhere, because of the different dosage forms for administering each such antiretroviral drug separately. This is particularly of importance in case of elderly patients.

Although HIV-1 infection can be cured by cocktail of drugs offered as highly active antiretroviral therapy (HAART), but the emergence of resistant human immunodeficiency virus has created a new challenge to combat the adverse situation of the disease. Resistance in the strains is a major cause of failure of antiretroviral therapy that may ultimately compromise the antiretroviral's efficacy in general population. In most cases, resistance is due to poor adherence by the patient and/or to low potency of the therapeutic regimen. Resistance may be primary or acquired. The combination of long treatment and side effects results in poor compliance, which is a major contributor to the development of resistance. Hence there is an obvious and urgent need to provide either new combination of new or existing antiretroviral drugs which will be eventually effective against drug resistant strains or to either improve the drug characteristics by improving bioavailability of the antiviral drugs as this will further reduce the dose and duration of treatment regimens and leading to patient compliance.

WO2011120133 discloses doravirine and its combinations with other HIV drugs such as etravirine, fosamprenavir calcium, indinavir, lamivudine, lamivudine+zidovudine, lopinavir, lopinavir+ritonavir, maraviroc, nelfinavir, nevirapine, raltegravir, ritonavir, saquinavir, stavudine, tenofovir DF, tipranavir, vicriviroc, abacavir, delavirdine, atazanavir.

A Dose-Ranging Study to Compare Doravirine (MK-1439) Plus TRUVADA® Versus Efavirenz Plus TRUVADA® in Human Immunodeficiency Virus (HIV)-1 Infected Participants (MK-1439-007).

Pharmacokinetic boosters or enhancers are used to boost the effectiveness of antiretroviral drugs. When a pharmacokinetic booster or enhancer is coadministered with an anti-retroviral drug, the pharmacokinetic enhancer interferes with the breakdown of the anti-retroviral drug, which causes the anti-retroviral drug to remain in the body for a longer time and at a higher concentration.

Pharmacokinetic boosters or enhancers specifically cause inhibition of the cytochrome P450 3A4 enzyme system leading to an increase in the plasma concentrations of the co-administered antiretroviral drugs. Protease Inhibitors are one such class of antiretroviral drugs that generally exhibit high genetic barrier for drug resistance and hence do require a pharmacokinetic booster or enhancer to be co-administered. Out of all the approved drugs for the treatment of HIV, Ritonavir and Cobicistat are termed as pharmacokinetic 'boosters or 'enhancers.

Besides ritonavir and cobicistat, there are many naturally occurring substances which are reported in literature and may be explored to improve the pharmacokinetic activity of certain drugs.

These naturally occurring substances which act as bioenhancers are chemical entities that promote and augment the bioavailability of the drugs which are mixed with them and do not exhibit synergistic effect with the drug. Examples of these bioenhancers include piperine, garlic, *Carum carvi*, Currinum cyrrinurn lysergol, naringin, quercetin, niaziridin, glycyrrhizin, stevia, cow urine, distillate ginger, etc.

These pharmacokinetic 'boosters or 'enhancers might reduce the cost of antiviral therapy, reduce pill burden for patients, and/or reduce the risk of sub therapeutic antiviral concentrations (e.g., development of resistance as well as enhance adherence to antiviral therapy).

Therefore, there remains a need to provide a new combination therapy of some antiretroviral drugs or combination therapy of antiviral drugs with pharmacokinetic booster or enhancer for the treatment of HIV which reduces the dose of such anti-retroviral drugs, side effects exhibited by these drugs as well as maintains the optimal concentration of the same. Further, use of a naturally occurring pharmacokinetic booster or enhancer would eliminate or reduce interactions with other non-HIV medications that would be concurrently administered.

Further for most of the therapeutic agents to produce systemic effects, the oral route still represents the preferred way of administration, owing to its several advantages and high patient compliance as compared to any other route of administration. Tablets and hard gelatin capsules still constitute a major portion of drug delivery systems that are currently available.

However, many patient groups such as the elderly, children, and patients who are mentally retarded, uncooperative, nauseated, or on reduced liquid-intake/diets have difficulties swallowing the dosage forms such as tablets and hard gelatin capsules. Further, those who are traveling or have little access to water are similarly affected.

Also, the route of drug administration, appearance, color, taste, tablet size and dosing regimen are most important parameters that govern patient compliance.

Especially, the geriatric and pediatric patients experience difficulty in swallowing larger sized tablets wherein large size tablet may result in esophageal damage due to its physical characteristics if it is not swallowed properly, which ultimately leads to poor patient compliance.

Also, oral administration of bitter drugs with an acceptable degree of palatability is a key issue for health care providers, especially for pediatric patients.

Further, there has been an enhanced demand for dosage forms that are more patient-friendly and patient compliant. Since the development cost of a new drug molecule is very high, efforts are now being made to focus on the development of new drug dosage forms for existing drugs with improved safety and efficacy together with reduced dosing frequency as well as which are cost-effective.

Although, different treatment methods and dosage regimens have been framed in order to increase the patient adherence for treatment of HIV, there still remains a critical need for developing improved dosage forms such as a kit composition or dosage form by which a patient is encouraged to adhere to his daily dosage regimen. The combination of antiretroviral drugs administered in a single unit dosage form may result in increased patient compliance as the pill burden is reduced and dosing schedules are simplified. However, not all compounds are suitable for administration in combinations as there are several factors that influence the feasibility of combinations such as the chemical instability of the compounds, size of the dosage unit, potential for antagonistic or merely additive activities of the combined compounds, and difficulties in achieving a suitable formulation.

Thus there is an unmet need to find therapeutic agents suitable for use in combination to provide suitable pharmaceutical compositions to treat HIV infection and simultaneously increase the patient compliance.

OBJECT OF THE INVENTION

The object of the invention is to provide a pharmaceutical composition which is a combination therapy comprising of at least one reverse transcriptase inhibitor.

Another object of the invention is to provide a pharmaceutical composition comprising of at least one non-nucleoside reverse transcriptase inhibitor, at least one nucleoside reverse transcriptase inhibitor and at least one nucleotide reverse transcriptase inhibitor.

Yet another object of the invention is to provide a pharmaceutical composition comprising of at least one non-nucleoside reverse transcriptase inhibitor, at least one nucleoside reverse transcriptase inhibitor and at least one nucleotide reverse transcriptase inhibitor and optionally a booster or enhancer.

Another object of the invention is to provide a pharmaceutical composition comprising of at least one non-nucleoside reverse transcriptase inhibitor, at least one nucleoside reverse transcriptase inhibitor and at least one nucleotide reverse transcriptase inhibitor and optionally a pharmacokinetic booster or enhancer with reduced side effects.

Yet another object of the invention is to provide a pharmaceutical composition comprising of at least one non-nucleoside reverse transcriptase inhibitor, at least one nucleoside reverse transcriptase inhibitor and at least one nucleotide reverse transcriptase inhibitor and optionally a pharmacokinetic booster or enhancer with reduced side effects and reduced dose.

Yet another object of the invention is to provide a composition comprising of at least one non-nucleoside reverse transcriptase inhibitor, at least one nucleoside reverse transcriptase inhibitor and at least one nucleotide reverse transcriptase inhibitor optionally a pharmacokinetic booster or enhancer optionally with one or more pharmaceutically acceptable excipients.

Yet another object of the invention is to provide a process for manufacturing the pharmaceutical composition comprising of at least one non-nucleoside reverse transcriptase inhibitor, at least one nucleoside reverse transcriptase inhibitor and at least one nucleotide reverse transcriptase inhibitor optionally a pharmacokinetic booster or enhancer optionally with one or more pharmaceutically acceptable excipients.

Yet another object of the present invention is to provide a method for prevention and treatment or prophylaxis of diseases caused by retroviruses, especially HIV infection or acquired immune deficiency syndrome and process for manufacturing the pharmaceutical composition comprising of at least one non-nucleoside reverse transcriptase inhibitor, at least one nucleoside reverse transcriptase inhibitor and at least one nucleotide reverse transcriptase inhibitor and optionally a pharmacokinetic booster or enhancer optionally with one or more pharmaceutically acceptable excipients.

SUMMARY OF THE INVENTION

According to an aspect of the present invention, there is provided a pharmaceutical composition comprising at least one non-nucleoside reverse transcriptase inhibitor or its salt, solvate, esters, derivatives, hydrate, enantiomer, polymorph or mixtures thereof in combination with at least one nucleoside reverse transcriptase inhibitor or its salt, solvate, ester, derivatives, hydrate, enantiomer, polymorph or mixtures thereof, and at least one nucleotide reverse transcriptase inhibitor or its salt, solvate, esters, derivatives, hydrate, enantiomer, polymorph or mixtures thereof and optionally a pharmacokinetic booster or enhancer.

According to another aspect of the invention there is provided a process for manufacturing of the pharmaceutical composition comprising at least one non-nucleoside reverse transcriptase inhibitor or its salt, solvate, esters, derivatives, hydrate, enantiomer, polymorph or mixtures thereof in combination with at least one nucleoside reverse transcriptase inhibitor or its salt, solvate, ester, derivatives, hydrate, enantiomer, polymorph or mixtures thereof and at least one nucleotide reverse transcriptase inhibitor or its salt, solvate, esters, derivatives, hydrate, enantiomer, polymorph or mixtures thereof and optionally a pharmacokinetic booster or enhancer.

According to another aspect of the invention, there is provided a method of prevention and treatment or prophylaxis of diseases caused by retroviruses, especially HIV infection or acquired immune deficiency syndrome and process for manufacturing the pharmaceutical composition comprising of at least one anti-retroviral agent and optionally a pharmacokinetic booster or enhancer with one or more pharmaceutically acceptable excipients.

DETAILED DESCRIPTION OF INVENTION

For the treatment of antiretroviral infections like HIV infection or acquired immunodeficiency syndrome, the drug should have high bioavailability with low dose leading to minimum side effects. Also, it is essential that the amount of drug reached its site of action. Thus, there is a need for such drugs or combination of drugs for better treatment of patients suffering from antiretroviral infection such as HIV.

Most antiretroviral drugs have either become ineffective to strains because of the resistant developed in the strains. Most antiretroviral drugs also have poor solubility and/or poor permeability which deteriorates the bioavailability of the drug to a major extent.

The inventors have found that a combination formulation of at least one non-nucleoside reverse transcriptase inhibitor, at least one nucleoside reverse transcriptase inhibitor and at least one nucleotide reverse transcriptase inhibitor having lesser side effects and significantly higher bioavailability which can optionally be used along with a pharmacokinetic booster or enhancer to provide a suitable pharmaceutical composition.

Reverse transcriptase inhibitors are a class of anti-retroviral compounds that inhibit the enzyme reverse transcriptase and thus inhibit synthesis of viral DNA in the host's cell. Inhibition of viral DNA synthesis prevents further replication of the HIV virus. Reverse transcriptase inhibitors can be classified into two main categories viz. Nucleoside reverse transcriptase inhibitors, nucleotide reverse transcriptase inhibitor and non-nucleoside transcriptase inhibitors. The term "nucleoside and nucleotide reverse transcriptase inhibitors" (NRTIs) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA. Nucleoside reverse transcriptase inhibitors are the first line of treatment for HIV infected patients. They are usually used with non-nucleoside reverse transcriptase inhibitors for synergistic effect.

Suitable nucleoside reverse transcriptase inhibitors (NRTIs) that may be employed in the pharmaceutical composition of the present invention may comprise zidovudine; didanosine; stavudine; lamivudine; abacavir; adefovir; lobucavir; entecavir; apricitabine; emtricitabine; zalcitabine; dexelvucitabine; alovudine; amdoxovir; elvucitabine; AVX754; BCH-189; phosphazid; racivir; SP 1093V; stampidine; BCH-10652, p-L-FD4 (also called -L-D4C and named P-L-2',3'-dicleoxy-5-fluoro-cytidene); DAPD, the purine nucleoside, (–)-P-D-2,6-diamino-purine dioxolane; and lodenosine (FddA), 9-(2,3-dideoxy-2-fluoro-D-threo-pentofiiranosyl)adenine or their salt, solvate, esters, derivatives, hydrate, enantiomer, polymorph prodrugs, tautomers, isomers, anhydrates or mixtures thereof and any combination thereof. Preferably, the nucleoside reverse transcriptase inhibitor is emtricitabine or its acceptable salt in the pharmaceutical composition of present invention.

Suitable nucleotide reverse transcriptase inhibitors (NtRTIs) that may be employed in the pharmaceutical composition of the present invention may comprise tenofovir and adefovir or their salt, solvate, esters, derivatives, hydrate, enantiomer, polymorph prodrugs, tautomers, isomers, anhydrates or mixtures thereof and any combination thereof.

Preferably, the nucleotide reverse transcriptase inhibitor is tenofovir or its acceptable salt in the pharmaceutical composition of present invention.

Suitable non-nucleoside reverse transcriptase inhibitors that may be employed in pharmaceutical composition of present invention may comprise, but are not limited to, Efavirenz, nevirapine, doravirine, delavirdine, etravirine, rilpivirine, or their salt, solvate, esters, derivatives, hydrate, enantiomer, polymorph prodrugs, tautomers, isomers, anhydrates or mixtures thereof and any combination thereof. Preferably, the non-nucleoside reverse transcriptase inhibitor is doravirine or its acceptable salt in the pharmaceutical composition of present invention.

Preferably, the present invention thus provides a pharmaceutical composition comprising doravirine in combination with tenofovir alafenamide fumarate and emtricitabine.

Preferably the dose of doravirine ranges from about 10 mg to 200 mg, tenofovir alafenamide ranges from about 1 mg to 25 mg and emtricitabine is 200 mg for once or twice a day administration.

The pharmaceutical composition of present invention may further comprises of other antiretroviral drugs such as non-nucleotide reverse transcriptase inhibitor, protease inhibitors (Pis), and maturation inhibitors (Mls) and any combination thereof.

Suitable non-nucleotide reverse transcriptase inhibitors (NNRTIs) that may be employed in the pharmaceutical composition of the present invention may comprise nevirapine, rilpivirine, delaviridine, efavirenz, etravirine. Other NNRTIs include PNU-142721, a fiiropyridine-thiopyrimide; capravirine (S-1153 or AG-1 549; 5-(3,5-dichlorophenyl)-thio-4-isopropyl-1-(4-pyridyl)methyl-1H-imidazol-2-ylmethyl carbonate); emivirine [MKC-442; (1-(ethoxy-memyl)-5-(1-methylethyl)-6-(phenylmethyl)-(2,4(1H,3H)-pyrimidinedione)]; (+)-calanolide A (NSC-67545 1) and B, coumarin derivatives; DAPY (TMC120; 4-{4-[4-((E)-2-cyano-vinyl)-2,6-dimethyl-phenylamino]-pyrimidin-2-ylamino-}-benzonitrile); BILR-355 BS (12-ethyl-8-[2-(1-hydroxy-quinolin-4-yloxy)-ethyl]-5-methyl-11,12-dihydro~5H-1,5,10,12-tetraaza-dibenzo[a,e]cycloocten-6-one; PHI-236 (7-bromo-3-[2-(2,5-dimethoxy-phenyl)-ethyl]-3,4-dihydro-1H-pyrido[1,2-a][-1,3,5]triazine-2-thione) and PHI-443 (TMC-278, 1-(5-bromo-pyridin-2-yl)-3-(2-thiophen-2-yl-ethyl)-thiourea) or their salt, solvate, esters, derivatives, hydrate, enantiomer, polymorph prodrugs, tautomers, isomers, anhydrates or mixtures thereof and any combination thereof. Suitable protease inhibitors (Pis) that may be employed in the pharmaceutical composition of the present invention may comprise saquinavir; ritonavir; nelfinavir; amprenavir; lopinavir, indinavir; nelfinavir; atazanavir; lasinavir; palinavir; tipranavir; fosamprenavir; darunavir; TMC114; DMP450, a cyclic urea; BMS-7322623, BMS-232623; GS3333; KNI-413; KNI-272; LG-71350; CGP-61755; PD 173606; PD 177298; PD 178390; PD 178392; U-140690; ABT-378; and AG-1549 an imidazole carbonate. Additional Pis include N-cycloalkylglycines, a-hydroxyarylbutanamides; a-hydro-y-[[(carbocyclic- or heterocyclic-substituted)amino)carbonyl]alkanamide derivatives; y-hydroxy-2-(fluoroalkylaminocarbonyl)-1-piperazinepentanamides; dihydropyrone derivatives and a- and β-amino acid hydroxyethylaminosulfonamides; and N-aminoacid substituted L-lysine derivatives.

Further, the pharmaceutical composition comprising combination of antiretroviral drugs viz non-nucleoside reverse transcriptase inhibitor, nucleotide reverse transcriptase inhibitor, nucleoside reverse transcriptase inhibitor and further comprises pharmacokinetic booster or enhancer.

The term 'Anti-retroviral drug_ and 'Pharmacokinetic booster or enhancer is used in broad sense to include not only 'Anti-retroviral drug per se and 'Pharmacokinetic booster or enhancer_ per se but also its pharmaceutically acceptable derivatives thereof. Suitable pharmaceutically acceptable derivatives include pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

The term "pharmacokinetic booster or enhancer" is an alkaloid. More preferably, the pharmacokinetic booster or enhancer includes, but is not limited to piperine, isopiperine, tetrahydropiperine, chavicine, isochavicine.

The fruit of black pepper (*Piper nigrum* L.) and long pepper (*Piper longum* L.) are both important medicinal herbs in Ayurvedic and Unani (traditional Indian) systems of medicine, wherein the remedy generally consists of mixtures of herbs. A wide range of the medicinal uses of black pepper are known and have been documented including its use in the treatment of leucoderma.

Piperine, the major alkaloid found in the fruit of black pepper (*Piper nigrum* L.; Piperaceae), stimulates the replication of melanocytes and induces the formation of melanocytic dendrites. Piperine is expected to cause the repopulation of vitiligo patches through a stimulatory effect on perilesional and follicular melanocytes.

Piperine is chemically known as (1-2E, 4E-piperinoyl-piperidine) and is structurally represented as below.

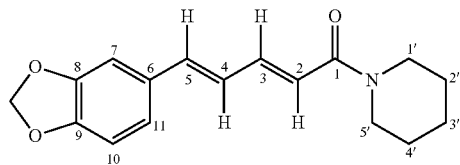

Piperine [E,E-(trans-trans)-piperine]

Piperine may enhance the drug bioavailability by promoting rapid absorption of drugs and nutrients by increasing blood supply to the gastrointestinal tract, decreasing hydrochloric acid secretion to prevent the breakdown of some drugs, increasing the emulsifying content of the gut, increasing enzymes like γ-glutamyl transpeptidase which participate in active and passive transport of nutrients to the intestinal cells.

Piperine may increase the drug bioavailability by inhibiting enzymes which participate in the biotransformation of drugs and thus preventing their inactivation and elimination. It also inhibits p-glycoprotein, the 'pump' protein that removes substances from cells and can decrease the intestinal production of glucuronic acid, thereby permitting more substances to enter the body in active form.

Piperine has also been reported to occur in other *Piper* species i.e. *P. acutisleginum, album, argyrophylum, attenuatum, aurantiacum, betle, callosum, chaba, cubeba, guineense, hancei, khasiana, longum, macropodum, nepalense, novae hollandiae, peepuloides, retrokacturn, sylvaticum.*

Tetrahydro piperine is a structural analog of Piperine. The two double bonds at position 2 and 4 are saturated to give a tetrahydro analog. Tetrahydropiperine is chemically known as 5-(1,3-benzodioxol-5-yl)-1-piperidin-1-ylpentan-1-one and is structurally represented as below.

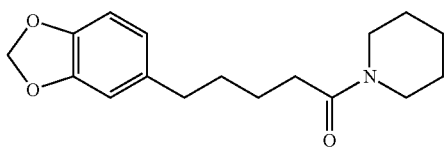 [SMILES: O=C(CCCCc1ccc2c(c1)OCO2)N1CCCCC1]

Tetrahydropiperine occurs like piperine naturally in black pepper (about 0.7% in black pepper oleoresin). Tetrahydropiperine can be synthesized from piperine which is previously extracted from black pepper oleoresin.

The term "analogs or derivatives" of tetrahydropiperine is used in broad sense to include alkyltetrahydropiperines, e.g. methyltetrahydropiperine or ethyltetrahydropiperine, dialkyltetrahydropiperines, e.g. dimethyltetrahydropiperine or diethyltetrahydropiperine, alkoxylated tetrahydropiperine, e.g. methoxy tetrahydropiperine, hydroxylated tetrahydropiperine, e.g. 1-[(5,3-benzodioxyl-5-yl)-1-hydroxy-2,4-pentadienyl]-piperine, 1-[(5,3-benzodioxyl-5-yl)-1-methoxy-2,4-pentadienyl]-piperine, halogenated tetrahydropiperine, e.g. 1-[(5,3-benzodioxyl-5-yl)-1-oxo-4-halo-2-pentenyl]-piperine and 1-[(5,3-benzodioxyl-5-yl)-1-oxo-2-halo-4-pentenyl]-piperine, dihydropiperine, alkyldihydropiperines, e.g. methyldihydropiperine or ethyldihydropiperine, dialkyldihydropiperines, e.g. dimethyldihydropiperine or diethyldihydropiperine, alkoxylated dihydropiperine, e.g. methoxy dihydropiperine, and halogenated dihydropiperine and their pharmaceutically acceptable salts, pharmaceutically acceptable solvates, pharmaceutically acceptable hydrates, pharmaceutically acceptable anhydrates, pharmaceutically acceptable enantiomers, pharmaceutically acceptable esters, pharmaceutically acceptable isomers, pharmaceutically acceptable polymorphs, pharmaceutically acceptable prodrugs, pharmaceutically acceptable tautomers, pharmaceutically acceptable complexes etc.

Preferably the dose of piperine ranges from about 0.5 mg to about 400 mg and the dose of tetrahydropiperine ranges from about 0.5 mg to about 400 mg.

In one embodiment, the dose of the piperine and/or the tetrahydropiperine ranges from about 0.5 mg, 1, 2, 3, 4, 5, 6, 7, 8, 9, 10, 15, 20, 25, 30, 35, 40, 45, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, to about 400 mg.

In one embodiment, present invention thus provides a pharmaceutical composition comprising doravirine, tenofovir alafenamide fumarate and emtricitabine with at least one pharmacokinetic enhancer or booster for once or twice a day administration.

In another embodiment, the ratio of the at least one anti-retroviral drug to the at least one pharmacokinetic booster or enhancer is from about 100:1 to about 1:1 by weight.

According to an embodiment, the pharmaceutical composition of present invention comprises of antiretroviral drugs such as doravirine, emtricitabine and tenofovir alafenamide fumarate and piperine in a ratio from about 100:1, 50:1, 40:1, 30:1, 20:1, 10:1, 8:1, 6:1, 5:1, 4:1, 3:1, 2:1, to about 1:1 by weight.

In some embodiments, the pharmaceutical compositions of the present invention comprises doravirine and piperine for the treatment of diseases caused by retrovirus, especially acquired immune deficiency syndrome or an HIV infection.

According to an embodiment, the pharmaceutical composition of present invention comprises of antiretroviral drugs such as doravirine and piperine in a ratio from about 100:1, 50:1, 40:1, 30:1, 20:1, 10:1, 8:1, 6:1, 5:1, 4:1, 3:1, 2:1, to about 1:1 by weight.

The term 'treatment' or 'treating' of a disease, virus or condition refers to executing a protocol that may include administering one or more drugs to a patient, in an effort to alleviate signs or symptoms of the disease, virus or condition. Alleviation can occur prior to signs or symptoms of the disease, virus or condition appearing, as well as after their appearance. Thus, treating or treatment includes reducing, preventing or prevention of the disease, virus or condition. In addition, treating or treatment does not require complete alleviation of signs or symptoms, does not require a cure, and specifically includes protocols that have only a marginal effect on the patient.

The present invention also provides for the respective therapeutic agents to be administered simultaneously or separately either in the same or different pharmaceutical compositions. If there is separate administration, the invention furthermore provides that the subsequently administered therapeutic agents should be administered to a patient within a time scale to achieve, or more particularly optimize, synergistic therapeutic effect of such a combined preparation.

In one embodiment, the pharmaceutical composition is administered via nanoparticles having a size of about 1 nanometer (nm) to about 50 nm.

The term "pharmaceutical composition" includes dosage forms such as but not limited to, unit dosage forms including tablets, capsules (filled with powders, pellets, beads, mini-tablets, pills, micro-pellets, small tablet units, multiple unit pellet systems (MUPS), disintegrating tablets, dispersible tablets, granules, and microspheres, multiparticulates), sachets (filled with powders, pellets, beads, mini-tablets, pills, micro-pellets, small tablet units, MUPS, disintegrating tablets, dispersible tablets, granules, and microspheres, multiparticulates), powders for reconstitution, transdermal patches and sprinkles, however, other dosage forms such as controlled release formulations, lyophilized formulations, modified release formulations, delayed release formulations, extended release formulations, pulsatile release formulations, dual release formulations and the like. Liquid or semisolid dosage form (liquids, suspensions, solutions, dispersions, ointments, creams, emulsions, microemulsions, sprays, patches, spot-on), injection preparations, parenteral, topical, inhalations, buccal, nasal etc. may also be envisaged under the ambit of the invention.

Preferably, the mini-tablets or granules filled in such hard gelatin capsules or sachets are directly administered or by sprinkling the mini-tablet or granules on regular meals. Alternatively, the mini-tablets or granules filled in hard gelatin capsules or sachets may be administered with liquid or semi-solid beverages such as but not limited to, juices, water.

The mini-tablets or granules, according to the present invention, may also optionally be coated. Preferably, mini-tablets or granules, according to the present invention, may be film coated. More preferably, the mini-tablets or granules may be seal coated and then film coated and further filled in hard gelatin capsules or sachets.

It is further well known in the art that a tablet formulation is the preferred solid dosage form due to its greater stability, less risk of chemical interaction between different medicaments, smaller bulk, accurate dosage, and ease of production.

Solid unit dosage forms, according to the present invention, are preferably in the form of tablets either single or bilayered or multilayered tablets but other conventional dosages such as powders, pellets, capsules and sachets may fall within the scope of this invention.

According to one embodiment, the antiretroviral composition may be administered simultaneously, separately or sequentially in a single unit dosage form. When the active ingredients are administered sequentially, either at least one anti-retroviral drug or piperine/tetrahydropiperine, may be administered first. When administration is simultaneous, the active ingredients may be administered either in the same or different pharmaceutical compositions. Adjunctive therapy, i.e. where one active ingredient is used as the primary treatment and the other active ingredient(s) is/are used to assist that primary treatment is also an embodiment of the present invention.

Accordingly, there is provided a pharmaceutical composition comprising doravirine, tenofovir alafenamide fumarate, emtricitabine and piperine and/or tetrahydropiperine or any of its derivatives as a combined preparation for simultaneous, separate or sequential use for treatment of diseases caused by retroviruses, especially HIV.

According to another embodiment, the pharmaceutical composition may be administered as a single layered or bilayererd or multilayered tablet wherein each layer may or may not contain drug/drugs along with pharmaceutically acceptable excipients which are then compressed to provide either a single layered, bilayered or multilayered tablet.

Suitable excipients may be used for formulating the various dosage forms according to the present invention such as, but not limited to, surface stabilizers or surfactants, viscosity modifying agents, polymers including extended release polymers, stabilizers, disintegrants or super disintegrants, diluents, plasticizers, binders, glidants, lubricants, sweeteners, flavoring agents, anti-caking agents, opacifiers, anti-microbial agents, antifoaming agents, emulsifiers, buffering agents, coloring agents, carriers, fillers, anti-adherents, solvents, taste-masking agents, preservatives, antioxidants, texture enhancers, channeling agents, coating agents or combinations thereof.

Accordingly, when the pharmaceutical composition is provided in unit dosage forms, as discussed above, the unit dosage form can be uncoated or coated.

The present invention provides method of prevention, treatment or prophylaxis of diseases caused by retroviruses, especially acquired immune deficiency syndrome or an HIV infection, which method comprises administering the pharmaceutical composition substantially as hereinbefore described.

There is further provided by the present invention an antiretroviral composition substantially as hereinbefore described, for use in treating disorders or conditions that respond to, or are prevented, ameliorated or eliminated by administering the pharmaceutical composition comprising substantially as hereinbefore described.

The following examples are for the purpose of illustration of the invention only and are not intended in any way to limit the scope of the present invention.

Example 1

| Sr No | Ingredients | Mg/tab | | | |
|---|---|---|---|---|---|
| I. | | Blending | | | |
| 1. | Emtricitabine | 200.00 | 200.00 | 200.00 | 200.00 |
| 2. | Tenofovir alafenamide fumarate | 28.045 | 28.045 | 28.045 | 28.045 |
| 3. | Doravirine | 25.00 | 50.00 | 100.00 | 200.00 |
| 4. | Microcrystalline cellulose | 80.005 | 100.005 | 120.005 | 140.005 |
| 5. | Croscarmellose sodium | 26.25 | 26.25 | 26.25 | 26.25 |
| II. | | Lubrication (Before Compaction) | | | |
| 6. | Magnesium Stearate | 2.700 | 2.700 | 2.700 | 2.700 |
| III. | | Blending (After Compaction) | | | |
| 7. | Microcrystalline cellulose | 15.000 | 15.000 | 15.000 | 15.000 |
| IV. | | Lubrication (After Compaction) | | | |
| 8. | Magnesium Stearate | 3.000 | 3.000 | 3.000 | 3.000 |
| | Total weight of Core tablet | 380.000 | 425.000 | 495.000 | 615.000 |
| V. | | Coating | | | |
| 9. | Opadry II 85F18422 White INH | 10.00 | 13.00 | 15.00 | 19.00 |
| 10. | Purified water | q.s | q.s | q.s | q.s |
| | Total weight of coated tablet | 390.00 | 438.00 | 510.00 | 634.00 |

Process:
1) Emtricitabine, Tenofovir alafemanide fumarate, Doravirine, Microcrystalline cellulose and Croscarmellose sodium, Magnesium stearate were sifted and blended.
2) The blend obtained in step (1) was compacted to achieve a desired particle size.
3) Microcrystalline cellulose and Magnesium stearate were sifted and added to the compact obtained in step (2).
4) The blend obtained in step (3) was compressed to prepare tablets and the tablets so obtained were coated.

Example 2

| Sr. No. | Ingredients | Mg/tab | | | |
|---|---|---|---|---|---|
| I | | Blending | | | |
| 1 | Emtricitabine | 200.00 | 200.00 | 200.00 | 200.00 |
| 2 | Tenofovir alafenamide fumarate | 28.045 | 28.045 | 28.045 | 28.045 |
| 3 | Doravirine | 25.00 | 50.00 | 100.00 | 200.00 |
| 4 | Piperine | 20.00 | 20.00 | 20.00 | 20.00 |
| 5 | Microcrystalline cellulose | 80.005 | 100.005 | 120.005 | 140.005 |
| 6 | Croscarmellose sodium | 26.25 | 26.25 | 26.25 | 26.25 |
| II | | Lubrication (Before Compaction) | | | |
| 7 | Magnesium Stearate | 2.700 | 2.700 | 2.700 | 2.700 |
| III | | Blending (After Compaction) | | | |
| 8 | Microcrystalline cellulose | 15.000 | 15.000 | 15.000 | 15.000 |
| IV | | Lubrication (After Compaction) | | | |
| 9 | Magnesium Stearate | 3.000 | 3.000 | 3.000 | 3.000 |
| | Total weight of Core tablet | 400.000 | 445.000 | 515.000 | 635.000 |
| V | | Coating | | | |
| 10 | Opadry II 85F18422 White INH | 12.00 | 13.00 | 15.00 | 19.00 |
| 11 | Purified water | q.s | q.s | q.s | q.s |
| | Total weight of coated tablet | 412.00 | 458.00 | 530.00 | 654.00 |

Process:
1) Emtricitabine, Tenofovir alafemanide fumarate, Doravirine, Piperine, Microcrystalline cellulose and Croscarmellose sodium, Magnesium stearate were sifted and blended.

2) The blend obtained in step (1) was compacted to achieve a desired particle size.
3) Microcrystalline cellulose and Magnesium stearate were sifted and added to the compact obtained in step (2).
4) The blend obtained in step (3) was compressed to prepare tablets and the tablets so obtained were coated.

It will be readily apparent to one skilled in the art that varying substitutions and modifications may be made to the invention disclosed herein without departing from the spirit of the invention. Thus, it should be understood that although the present invention has been specifically disclosed by the preferred embodiments and optional features, modification and variation of the concepts herein disclosed may be resorted to by those skilled in the art, and such modifications and variations are considered to be falling within the scope of the invention.

It is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It must be noted that, as used in this specification and the appended claims, the singular forms "a," "an" and "the" include plural references unless the context clearly dictates otherwise.

We claim:

1. A pharmaceutical composition comprising: (i) doravirine; and (ii) at least one pharmacokinetic booster or enhancer selected from the group consisting of: piperine, tetrahydropiperine, cis-piperine, trans-piperine, cis-trans piperine, trans,cis-piperine, cis,cis-piperine, trans,trans-piperine and any combination thereof.

2. The pharmaceutical composition of claim 1, further comprising: at least one non-nucleoside reverse transcriptase inhibitor selected from the group consisting of: efavirenz, nevirapine, delavirdine, etravirine, rilpivirine and any combination thereof.

3. The pharmaceutical composition of claim 1, further comprising: at least one nucleoside reverse transcriptase inhibitor (NRTI) selected from a group consisting of: zidovudine; didanosine; stavudine; lamivudine; abacavir; adefovir; lobucavir; entecavir; apricitabine; emtricitabine; zalcitabine; dexelvucitabine; alovudine; amdoxovir; elvucitabine; AVX754; BCH-189; phosphazid; racivir; SP 1093V; stampidine; BCH-10652, p-L-FD4 (also called -L-D4C and named P-L-2',3'-dicleoxy-5-fluoro-cytidene); DAPD, the purine nucleoside, (−)-P-D-2,6-diamino-purine dioxolane; and lodenosine (FddA), 9-(2,3-dideoxy-2-fluoro-D-threo-pentofiiranosyl)adenine and any combination thereof.

4. The pharmaceutical composition of claim 1, further comprising at least one nucleotide reverse transcriptase inhibitor selected from the group consisting of: tenofovir, adefovir and any combination thereof.

5. The pharmaceutical composition of claim 1, wherein the composition comprises one or more pharmaceutically acceptable excipients selected from carriers, diluents, fillers, binders, lubricants, glidants, disintegrants, bulking agents, flavourants or any combination thereof.

6. The pharmaceutical composition of claim 1 wherein doravirine is present in the composition at a dose from about 10 mg to 200 mg, and further comprising tenofovir alafenamide at a dose from about 1 mg to 25 mg and lamivudine at a dose from about 300 mg for once or twice a day administration.

7. The pharmaceutical composition of claim 1 wherein doravirine is present in the composition at a dose from about 10 mg to 200 mg, and further comprising tenofovir alafenamide at a dose from about 1 mg to 25 mg and emtricitabine at a dose from about 200 mg for once or twice a day administration.

8. The pharmaceutical composition of claim 1 is in the form of a tablet, mini-tablet, granules, sprinkles, capsules, sachets, powders, pellets, an injectable composition in the form of a solution, suspension, emulsion, lyophilized powder or in the form of a kit.

9. The pharmaceutical composition of claim 1, wherein the pharmaceutical composition is formulated for administration to a patient in need thereof in the treatment or prophylaxis of diseases caused by retroviruses.

10. The pharmaceutical composition according to claim 1 further comprising a therapeutically effective amount of at least one non-nucleoside reverse transcriptase inhibitor, at least one nucleoside reverse transcriptase inhibitor and at least one nucleotide reverse transcriptase inhibitor and optionally one or more pharmaceutically acceptable excipients further comprising at least one pharmacokinetic booster or enhancer or derivative thereof.

11. The pharmaceutical composition of claim 1, wherein the at least one pharmacokinetic booster comprises piperine in the composition in an amount of from about 0.5 mg to about 400 mg.

12. The pharmaceutical composition of claim 1, wherein the ratio of doravirine to the at least one pharmacokinetic booster or enhancer or derivative thereof is from about 100:1 to about 1:1 by weight.

13. The pharmaceutical composition of claim 1, wherein (i) the at least one pharmacokinetic booster or enhancer or derivative thereof reduces a dosing frequency of doravirine that is administered to a patient; and (ii) the at least one pharmacokinetic booster or enhancer or derivative thereof increases the bioavailability of the doravirine from about 10% to about 70%.

14. The pharmaceutical composition of claim 1, wherein the composition is in the form of a tablet, mini-tablet, granules, sprinkles, capsules, sachets, powders, pellets, an injectable composition in the form of a solution, suspension, emulsion, lyophilized powder or in the form of a kit.

15. A pharmaceutical composition comprising doravirine, tenofovir alafenamide, emtricitabine, piperine and optionally pharmaceutically acceptable excipients.

16. The pharmaceutical composition of claim 15, wherein the pharmaceutical composition is formulated for administration to a patient in need thereof in the treatment or prophylaxis of diseases caused by retroviruses.

17. A method of treating diseases caused by retroviruses in a patient in need of such treatment, the method comprising: administering to a patient in need thereof a pharmaceutical composition comprising (i) doravirine; (ii) a therapeutically effective amount of at least one pharmacokinetic booster or enhancer or derivative thereof selected from the group consisting of: piperine, tetrahydropiperine, cis-piperine, trans-piperine, cis-trans piperine, trans,cis-piperine, cis, cis-piperine, trans,trans-piperine and any combination thereof; and (iii) one or more pharmaceutically acceptable excipients comprising carriers, diluents, fillers, binders, lubricants, glidants, disintegrants, bulking agents, flavourants or any combination thereof.

18. The method according to claim 17, wherein the diseases caused by retroviruses comprises acquired immune deficiency syndrome or an HIV infection.

19. A kit for treating disease caused by retroviruses, the kit comprising doravirine, and (ii) at least one pharmacokinetic booster or enhancer or derivative thereof selected from the group consisting of: piperine, tetrahydropiperine, cis-piperine, trans-piperine, cis-trans piperine, trans,cis-piperine, cis, cis-piperine, trans,trans-piperine and a combination thereof, wherein doravirine and the pharmacokinetic booster or enhancer or derivative thereof are in a separate composition respectively.

20. A kit for treating disease caused by retroviruses, the kit comprising a therapeutically effective amount of doravirine and a therapeutically effective amount of at least one pharmacokinetic booster or enhancer selected from the group consisting of: piperine, tetrahydropiperine, cis-piperine, trans-piperine, cis-trans piperine, trans,cis-piperine, cis,cis-piperine, trans,trans-piperine and a combination thereof, wherein the doravirine is in a separate composition from the at least one pharmacokinetic booster or enhancer.

21. A method of enhancing the bioavailability of doravirine, the method comprising providing a therapeutically effective amount of doravirine and providing a therapeutically effective amount of at least one pharmacokinetic booster or enhancer selected from the group consisting of: piperine, tetrahydropiperine, cis-piperine, trans-piperine, cis-trans piperine, trans,cis-piperine, cis,cis-piperine, trans, trans-piperine and any combination thereof.

22. The method of claim 21, wherein (i) the doravirine is in a first composition and the at least one pharmacokinetic booster or enhancer is in a second composition; or (ii) doravirine and the at least one pharmacokinetic booster or enhancer is combined in one composition.

23. A pharmaceutical composition comprising:
(i) a therapeutically effective amount of at least one non-nucleoside reverse transcriptase inhibitor selected from the group consisting of: efavirenz, nevirapine, doravirine, delavirdine, etravirine, rilpivirine and any combination thereof,
(ii) at least one nucleoside reverse transcriptase inhibitor,
(iii) at least one nucleotide reverse transcriptase inhibitor, and optionally one or more pharmaceutically acceptable excipients; and
(iv) at least one pharmacokinetic booster selected from the group consisting of: piperine, tetrahydropiperine, cis-piperine, trans-piperine, cis-trans piperine, trans, cis-piperine, cis,cis-piperine, trans,trans-piperine and any combination thereof.

* * * * *

UNITED STATES PATENT AND TRADEMARK OFFICE
CERTIFICATE OF CORRECTION

PATENT NO. : 11,234,981 B2
APPLICATION NO. : 16/606021
DATED : February 1, 2022
INVENTOR(S) : Geena Malhotra et al.

It is certified that error appears in the above-identified patent and that said Letters Patent is hereby corrected as shown below:

In the Specification
Column 7, Line 53-54, replace "BMS-7322623" with --BMS-2322623--.
Column 7, Line 57, replace "carbonate" with --carbamate--.
Column 7, Line 58, replace "a-hydro-y-" with --a-hydroxy-y- --.

Signed and Sealed this
Thirty-first Day of May, 2022

Katherine Kelly Vidal
*Director of the United States Patent and Trademark Office*